United States Patent [19]

Ariga et al.

[11] Patent Number: 5,773,262
[45] Date of Patent: Jun. 30, 1998

[54] PROCESS FOR THE PREPARATION OF PROANTHOCYANIDINS

[75] Inventors: Toshiaki Ariga, Noda; Hiroshi Hosoyama, Tokyo; Katsumi Yuasa, Funabashi, all of Japan

[73] Assignee: Kikkoman Corporation, Noda, Japan

[21] Appl. No.: 796,416

[22] Filed: Feb. 6, 1997

[30] Foreign Application Priority Data

Feb. 14, 1996 [JP] Japan ................................. 8-049664

[51] Int. Cl.⁶ .......................... C12P 17/16; C12P 17/18; C12P 17/06
[52] U.S. Cl. ...................... 435/118; 435/119; 435/125; 435/155; 435/267; 426/540; 426/545; 210/651; 210/663; 549/354; 549/355
[58] Field of Search ................... 435/155, 267, 435/118, 119, 125; 210/651, 663; 426/540, 545; 549/354, 355

[56] References Cited

U.S. PATENT DOCUMENTS 4,320,009  3/1982  Hilton et al. ........................ 210/651

OTHER PUBLICATIONS

Database WPI, AN 88–318 079, Derwent Publications, Ltd., London; & JP-A-63 233 799 (EISAI CO Ltd.) Abstract.

Soviet Patents Abstracts, B Section, week 8805, 1985, Aug. 30, Derwent Publications, Ltd., London; & SU-A-1317 027 (Moscow Lomonosov Univ.).

CA 123–312608(23) Kovac et al "Am J EnolVitic" 46,3, 1995 pp. 363–367.

Biotech 92–08652 Ohba et al "Appl. Microbiol Tech" 37,2, 176–179 (1992).

Japio ABS Nagao et al JO9051791 Feb. 25, 1997.

*Primary Examiner*—Herbert J. Lilling
*Attorney, Agent, or Firm*—Banner & Witcoff, Ltd.

[57] ABSTRACT

The present invention aims at enhancing purity of the proanthocyanidin extracts by acting yeast to the proanthocyanidin extracts for fermenting them to thereby assimilate the impurities such as saccharides with yeast to reduce them.

3 Claims, No Drawings

PROCESS FOR THE PREPARATION OF PROANTHOCYANIDINS

BACKGROUND OF THE INVENTION

1. Field of the Invention

The present invention relates to a process for preparing proanthocyanidins in a high yield through a yeast fermentation of proanthocyanidin extracts.

2. Description of the Related Art

Proanthocyanidins are a group of compounds comprising, as constitutional units, condensed type tannin existing in various plants, namely flavan-3-ols and flavan-3,4-diols, which are bonded by condensation or polymerization. Since these compounds are transformed into anthocyanidins such as cyanidin, delphinidin and pelargonidin by an acid treatment, they are called by the above name. The compounds include proanthocyanidins such as higher molecular procyanidin, prodelphinidin and propelargonidin, and their stereoisomers, which are dimers, trimers, tetramers, or decamers of said constitutional units.

The present inventors had discovered that these proanthocyanidins had a strong antioxidative activity, and filed a patent application on this discovery (Patent Kokoku No. 3-7232).

Proanthocyanidins can be obtained by extracting from various species of plants with water or an organic solvent such as ethanol or acetone, but analyses of the extracts confirmed presence of other substances than the preferred proanthocyanidins, such as crude proteins, carbohydrates and ash. Therefore, if an extract solution is directly concentrated and made into powder, there would remain a substantial amount of said substances as impurities in the product, which may cause a decreased commercial value of the product.

Analysis of carbohydrates of a proanthocyanidin extract from grape seeds showed that the main constituents of the extract were fructose and glucose. Considering that it should be possible to enhance purity of proanthocyanidins by removing these saccharides from the extract, the present inventors have pursued studies in this line and found that the desired effect could be obtained by subjecting the proanthocyanidin extract to a fermentation treatment with yeast. It was further found that heavy metals contained in the extract could be also assimilated by this treatment and the purifying effects could be obtained by reduction of heavy metal content.

The present invention has been attained on the basis of the above finding.

SUMMARY OF THE INVENTION

The present invention provides a process for preparing proanthocyanidins which comprises adding yeast to a proanthocyanidin extract to cause its fermentation, and subjecting the fermented extract to solid-liquid separation.

A detailed explanation of the present invention is given below.

The proanthocyanidin extracts which fall within the conception of the present invention include the extract liquids containing proanthocyanidins extracted from various plant sources such as grape seeds, grape skins cranberries, apples, adzuki beans, and the barks of *matsu* (pine), Japanese ceder and Japanese cypress with water or an organic solvent, concentrated liquid thereof, and aqueous solutions formed by redissolving the dried and powdered concentrate in water. These solutions contain proanthocyanidins in amount of at least 10% calculated on dry basis.

In case extraction has been conducted using water or hydrous ethanol, the extract may be used directly in the form as it is or after concentration, but in case extraction has been carried out with acetone and the like, it needs to remove acetone or such by concentration.

As the yeast to be added to the proanthocyanidin extract for fermentation, there can be used, for instance, those belonging to the genera Saccharomyces and Zygosaccharomyces, which include commercially available wine yeast, *sake* yeast and baker's yeast.

The yeast may be added and acted at a temperature and pH optimal for the action of the yeast used; for instance, the yeast may be added by adjusting the temperature of the proanthocyanidin extract to 5°–35° C. and its pH to 3–6. The fermentation time is 12 hours or more, preferably 24 hours or more.

The amount of yeast added is $10^4$–$10^8$ cells, preferably $10^5$–$10^7$ cells, per ml of the extract.

As a consequence of the above treatment, the saccharides in the proanthocyanidin extract are utilized by yeast to give an alcohol, so that the proanthocyanidin products obtained by concentrating and drying the extract after yeast fermentation have a lower amount of impurities and have a high proanthocyanidin content.

In case yeast fermentation is insufficient due to the lack of saccharide in the extract, saccharide may be added to the extract. In this way, the impurities such as heavy metals in the extract can be reduced through assimilation.

Of course, these products may be subjected to additional purification. In this case, since the substantial part of the impurities has already been removed, purification can be performed in a very simple way.

The present invention is further specifically illustrated by the following examples. The quantitative determination of proanthocyanidins was carried out according to R. Jambunathan et al method (J. Agric. Food Chem., 34, 425–429, 1986): A prothocyanidin-containing sample is heated in the presence of dilute hydrochloric acid to redden proanthocyanidin, and it is quantified from the measurement of absorbence at 550 nm and calibration curve drawn up using as standard a procyanidin tetramer separated and purified from cider according to A.G.H. Lea method (J. Sci. Food Agric., 34, 471–477, 1978).

Heavy metals were quantified by colorimetry using sodium sulfide, and the amount was calculated on the lead basis.

DESCRIPTION OF THE PREFERRED EMBODIMENTS

EXAMPLE 1

One kg of seeds of grape (species: Koshu) were extracted in 2 liters of 20% ethanol with stirring at 25° C. for one week followed by solid-liquid separation and addition of water to obtain 4 liters of a clear solution (alcohol concentration: 9%).

This clear solution was divided into two equal portions, and yeast (powdery wine yeast produced by Lallemand Inc. EC1118) was added to one portion to a concentration of 300 ppm to carry out stationary fermentation at 25° C. for 7 days, after which the solution was subjected to solid-liquid separation according to conventional method to obtain about 2 liters of clear solution.

This clear solution was concentrated and freeze-dried to produce a proanthocyanidin powder.

The other portion (2 liters) of the clear solution was used as control, and it was concentrated and freeze-dried with no yeast added thereto to obtain a proanthocyanidin powder.

The results are shown in Table 1.

TABLE 1

|  | Present invention | Control |
| --- | --- | --- |
| Yield of powdery product | 6.65 g | 9.50 g |
| Proanthocyanidin content in product | 51.0% | 35.7% |
| Heavy metal content in product | 2 ppm | 19 ppm |

EXAMPLE 2

Two kg of seeds of grape (species: Chardonnay) were extracted with 90° C. hot water for 2 hours, and after solid-liquid separation, the solution was concentrated under reduced pressure to obtain 1,200 ml of a concentrated solution with 10% solid content. This solution was divided into two equal portions, and *sake* yeast (Japan Brewage Association Yeast #7) was added to one portion in an amount of $1 \times 10^7$ cells per ml of the concentrated solution to carry out a fermentation at 20° C. for 2 days, followed by the same treatments as in Example 1 to obtain a proanthocyanidin powder. The other portion of the solution, used as control, was concentrated and freeze-dried without adding yeast to obtain a powdery product. The results are shown in Table 2.

TABLE 2

|  | Present invention | Control |
| --- | --- | --- |
| Yield of powdery product | 58.5 g | 89.6 g |
| Proanthocyanidin content in product | 59.0% | 32.0% |
| Heavy metal content in product | 2 ppm | 15 ppm |

EXAMPLE 3

100 g of a powdery grape seed extract (proanthocyanidin content in the powder: 41%) was dissolved in 2 liters of a 10% ethanol solution, to which 600 ppm of powdery wine yeast (Lalvin KI by Lallemand Inc.) was added to carry out a fermentation at 25° C. for 7 days, followed by solid-liquid separation, concentration and freeze-drying in the same way as in Example 1 to obtain 101 g of a powdery product. The proanthocyanidin content in this product was determined to be 61%, which represents about 50% improvement of the degree of purification.

EXAMPLE 4

100 g of powdery grape seed extract (proanthocyanidin content in the powder: 38%) was dissolved in one liter of water, to which powdery wine yeast (Lalvin L2226 by Lallemand Inc.) was added in an amount of 300 ppm to carry out a fermentation at 30° C. for 5 days, followed by solid-liquid separation, concentration and freeze-drying according to Example 1 to obtain 100 g of a powdery product. Analysis determined the proanthocyanidin content in the product was 54%, corresponding to about 42% improvement of the degree of purification.

According to the present invention, it is possible to enhance purity of proanthocyanidin preparations and to reduce heavy metals and other impurities therein by yeast fermentation to the proanthocyanidin extracts obtained from various plant sources.

What is claimed is:

1. A process for preparing a purified proanthocyanidin which comprises extracting plants containing proanthocyanidins with water or an organic solvent to obtain a proanthocyanidin extract, adding yeast to said proanthocyanidin extract, or a concentrated extract thereof, to assimilate sugars and heavy metals contained in said extract or concentrated extract and form a yeast-treated extract, and then concentrating and drying the yeast-treated extract.

2. A process for preparing a purified proanthocyanidin which comprises extracting grape seeds with hot water or aqueous alcohol to obtain a proanthocyanidin extract, adding yeast to said proanthocyanidin extract, or a concentrated extract thereof, to assimilate sugars and heavy metals contained in said extract or concentrated extract and form a yeast-treated extract, and then concentrating and drying the yeast-treated extract.

3. A process for preparing a purified proanthocyanidin which comprises extracting plants containing proanthocyanidins with water or an organic solvent to obtain a proanthocyanidin extract, optionally concentrating said extract, adding yeast to said proanthocyanidin extract, or said optionally concentrated extract, conducting a fermentation to assimilate sugars and heavy metals contained in said extract or concentrated extract and form a yeast-treated extract, removing the yeast from said yeast-treated extract and then concentrating and drying the yeast-treated extract.

* * * * *